United States Patent
Mathies et al.

(10) Patent No.: US 6,361,671 B1
(45) Date of Patent: Mar. 26, 2002

(54) MICROFABRICATED CAPILLARY ELECTROPHORESIS CHIP AND METHOD FOR SIMULTANEOUSLY DETECTING MULTIPLE REDOX LABELS

(75) Inventors: Richard A. Mathies, Moraga; Pankaj Singhal, Berkeley; Jin Xie, Walnut Creek; Alexander N. Glazer, Orinda, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/229,386

(22) Filed: Jan. 11, 1999

(51) Int. Cl.[7] .............................................. G01N 27/26
(52) U.S. Cl. ....................... 204/452; 204/603; 204/409; 422/70; 210/656
(58) Field of Search ................................ 204/451, 452, 204/601, 603, 400, 409, 411, 412; 422/70; 210/656

(56) References Cited

U.S. PATENT DOCUMENTS

| | | | | |
|---|---|---|---|---|
| 5,194,133 A | * | 3/1993 | Clark et al. ................. | 204/608 |
| 6,027,890 A | * | 2/2000 | Nees et al. ..................... | 435/6 |
| 6,045,676 A | * | 2/2000 | Mathies et al. ............. | 204/603 |

FOREIGN PATENT DOCUMENTS

| | | | | |
|---|---|---|---|---|
| WO | WO95/10040 | 4/1995 | ......... | G01N/27/447 |
| WO | WO97/12995 | 4/1997 | ............ | C12Q/1/68 |
| WO | WO98/09161 | 3/1998 | ......... | G01N/27/447 |
| WO | WO98/49549 | 11/1998 | .......... | G01N/27/26 |

OTHER PUBLICATIONS

Wolfgang Buchberger ("Electrochemical detectors—tailor-made techniques for liquid chromatography and capillary electrophoresis?", Fresenius J. Anal. Chem. (1996), 354:797–802).*

Caplus abstract of Kubab et al. ("4–bromomethyl–6–nitro–7–methoxycoumarin as an electrochemical label for carboxylic acids in liquid chromatographic detection", Analusis (1986), 14(3), 125–30).*

Caplus abstract of Swanek et al. ("Capillary electrophoresis with DNA derivatization and electrochemical detection for the analysis of cellular amino acids", J. Microcolumn Sep. (1998), 10(2), 185–192).*

Singhal et al., "Direct Electrochemical Detection of Purine– and Pyrimidine–Based Nucleotides with Sinusoidal Voltammetry," *Analytical Chemistry*, vol. 69, No. 17, Sep. 1, 1997, pp. 3552–3557.

* cited by examiner

*Primary Examiner*—Jill Warden
*Assistant Examiner*—Alex Noguerola
(74) *Attorney, Agent, or Firm*—Flehr Hohbach Test Albritton & Herbert LLP

(57) ABSTRACT

This invention relates to a microfabricated capillary electrophoresis chip for detecting multiple redox-active labels simultaneously using a matrix coding scheme and to a method of selectively labeling analytes for simultaneous electrochemical detection of multiple label-analyte conjugates after electrophoretic or chromatographic separation.

46 Claims, 10 Drawing Sheets

Oxidation Potentials
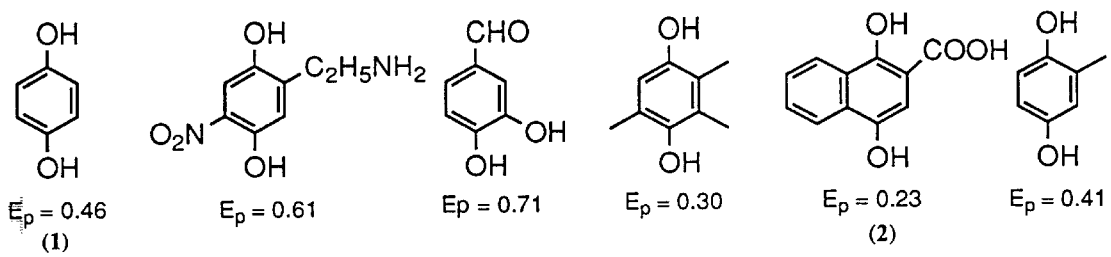
Reduction Potentials
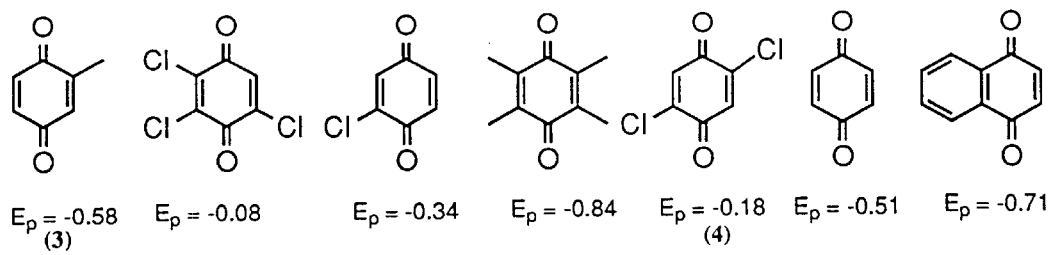
FIGURE 2
| Applied Potential | LABEL | | | |
|---|---|---|---|---|
| | 1 | 2 | 3 | 4 |
| +V1 | 0 | +1 | - | - |
| +V2 | +1 | +1 | - | - |
| -V3 | - | - | 0 | -1 |
| -V4 | - | - | -1 | -1 |
FIGURE 3

| Applied Potential | LABEL | | | |
|---|---|---|---|---|
|  | 1 | 2 | 3 | 4 |
| $V_1$ | 1 | 0 | 0 | 0 |
| $V_2$ | 1 | 1 | 0 | 0 |
| $V_3$ | 1 | 1 | 1 | 0 |
| $V_4$ | 1 | 1 | 1 | 1 |

Active ester of 1,4-Dihydroquinone Derivative (label 1)

Active ester of 2,5-Dichloro-1,4-Benzoquinone Derivative (label 3)

Active ester of 1,4-Benzoquinone Derivative (label 4)

Active ester of metalloporphyrins

MICROFABRICATED CAPILLARY ELECTROPHORESIS CHIP AND METHOD FOR SIMULTANEOUSLY DETECTING MULTIPLE REDOX LABELS

GOVERNMENT SUPPORT

This invention was made with Government support under Contract No. FG03-91ER61125 awarded by the United States Department of Energy. The Government has certain rights to this invention.

Brief Description of the Invention

This invention relates to a microfabricated capillary electrophoresis chip for detecting multiple redox-active labels simultaneously using a matrix coding scheme and to a method of selectively labeling analytes for simultaneous electrochemical detection of multiple label-analyte conjugates after electrophoretic or chromatographic separation.

BACKGROUND OF THE INVENTION

Capillary Electrophoresis (CE) is proving to be a powerful tool for DNA-sequencing and fragment sizing due to its low sample volume requirements, higher efficiency and rapidity of separations compared to the traditional approach of slab gel electrophoresis (Swerdlow, H. and Gesteland, R., (1990) *Nucl. Acid. Res.* 18, 1415–1419) (Kheterpal, I., Scherer, J. R., Clark, S. M., Radhakrishnan, A., Ju. J., Ginther, C. L., Sensabaugh, G. F. and Mathies, R. A., (1996) *Electrophoresis* 17, 1852–1859). More recently, microfabricated CE devices and Capillary Array Electrophoresis (CAE) microplates have demonstrated their potential for rapid, parallel separation of DNA sizing and sequencing samples (Woolley, A. T. and Mathies, R. A., (1994) *Proc. Natl. Acad. Sci. U.S.A.* 91, 11348–11352) (Woolley, A. T. and Mathies, R. A., *Anal. Chem.* 67, 3676–3680, 1995) (Woolley, A. T., Sensabaugh, G. F., and Mathies, R. A., (1997) *Anal. Chem.* 69, 2256–2261) (Simpson, P. C., Roach, D., Woolley, A. T., Thorsen, T., Johnston, R., Sensabaugh, G. F. and Mathies, R. A., (1998) *Proc. Natl. Acad Sci. U.S.A.* 95, 2256–2261). The development of these miniaturized CE platforms has been driven by the concept of making fully integrated, inexpensive and portable analytical systems.

Electrochemical (EC) detection is an approach which is easily adaptable to miniaturized CE platforms without any sacrifice in sensitivity or selectivity. EC detection has been widely used with conventional CE in fused-silica capillaries for highly sensitive and selective detection of various analytes. A critical problem in this application is figuring out how to decouple the high electrophoretic separation currents from the electrochemical detection system. Wallingford and Ewing first described the use of an on-column fracture with a porous glass-flit to decouple the high electrophoresis currents from the small electrochemical signals (Wallingford, R. A. and Ewing, A. G., (1987) *Anal. Chem.* 59, 1762–1766). The porous frit provided a way to ground the electrophoresis current prior to the detector electrode which was poised at the outlet of the capillary. The analytes in the buffer were pumped to the detector electrode by the residual electroosmotic flow existing in the capillary. Due to effective decoupling of the separation electric field from the detector electrode, this scheme allowed highly sensitive detection of the analytes. However, this system was very fragile due to the delicate porous glass frit, and it was difficult to align the electrode at the outlet of the capillary. A number of other designs have since been used to isolate the electrophoresis current which include porous nafion tubing (O'Shea, T. J., Greenhagen, R. D., Lunte, S. M., Lunte, C. E., Smyth, M. R., Radzik, D. M. and Watanabe, N., (1992) *J. Chromatogr.* 593, 305–312), and palladium joints (Kok, W. T., and Sahin, Y., (1993) *Anal. Chem.* 65, 2497–2501). All these designs are very fragile and not amenable for the construction of a robust CE-EC system. End-column detection in small diameter capillaries was then proposed as an alternative to the on-column fracture designs (Huang, X. H., Zare, R. N., Sloss, S., and Ewing, A. G., (1991) *Anal. Chem.* 63, 189–192). This approach capitalized on the fact that smaller inner diameter (<10 $\mu$m) capillaries exhibit very low electrophoretic currents due to their much smaller area. Thus, no isolation was required for the electrophoresis current, thereby obviating the need for any on-column current decouplers. EC detection has been successfully used as a detection method for capillary electrophoresis in fused-silica capillaries as small as 2 $\mu$m in diameter (Olefirowicz, T. M. and Ewing, A. G., (1990) *Anal. Chem.* 62, 1872–1876), with detection limits for various analytes in the femtomole to attomole mass range. Smaller diameter electrophoretic capillaries require the use of smaller diameter electrodes, or microelectrodes. Background noise is lower at these microelectrodes due to a sharp decrease in background charging currents (Bard, A. J. and Faulkner, L. R., (1980) *Electrochemical Methods:Fundamentals and Applications*, New York, John Wiley and Sons). This leads to better concentration sensitivity due to the higher signal-to-noise ratio. Mass sensitivity is also enhanced at these microelectrodes over bigger electrodes due to higher coulometric efficiency (Huang, X. H. et al., supra). End-column detection therefore allows the CE-EC approach to be performed successfully without any loss in sensitivity. However, very expensive micropositioners are required in order to accurately position microelectrodes at the outlet of such small diameter capillaries. Consequently, run-to-run reproducibility is very poor using this design. Many researchers have tried various ways of gluing an electrode in place outside a CE-capillary (Fermier, A. M., Gostkowski, M. L., and Colon, L. A., (1996) *Anal. Chem.* 68, 1661–1664) (Chen, M. C. and Huang, H. J., (1997) *Anal. Chem. Acta.* 341, 83–90), but this approach is still very tedious and irreproducible with very small diameter capillaries. It is also very hard to reliably make a large number of such assemblies with the same capillary-electrode alignment. Thus, end-column detection with conventional capillaries and electrodes is not useful for routine and automated analyses.

Microfabrication of electrodes at the outlet of microfabricated channels makes it possible to routinely perform end-column detection as the electrodes can be permanently fabricated with high precision and reproducibility. An approach to CE-EC detection on fully microfabricated systems was illustrated recently by Woolley et al. (Woolley, A. T., Lao, K., Glazer, A. N. and Mathies, R. A., (1998) *Anal. Chem.* 70, 684–688). Platinum microelectrodes were fabricated at the outlet of a CE-channel etched in a glass plate so as to allow effective isolation of the detection system from the electrophoresis currents in an end-column detection format. Sensitive detection of neurotransmitters with detection limits in the attomole range was accomplished with high reproducibility. The feasibility of using microfabricated capillary electrophoresis chips with integrated electrochemical detection to perform high-sensitivity DNA restriction fragment analysis and PCR product sizing was also demonstrated. DNA fragments were indirectly detected by adding an electroactive intercalator, iron-phenanthroline in the electrophoresis buffer. A $\phi$x HAE-III restriction digest was detected using this approach. The detection limit for the 603 base pair (bp) fragment was around 30 zeptomoles, and a PCR product from Salmonella was sized easily against an internal restriction fragment standard. This illustrates that microfabricated CE-EC systems are capable of highly sensitive detection.

However, indirect detection is not suitable for the selective detection of certain typical analytes in a complex mixture, as it is not specific to the detection of the desired analytes. Furthermore, since there was only one indirect and non-covalent redox active label in our previous work, it was more difficult to compare the size of an unknown DNA fragment with that or a standard because the signals can overlap. Direct labeling of analytes is typically needed to achieve selective simultaneous multiplex detection of various analytes. For example, in the case of fluorescence based DNA-sequencing, four different fluorescent labels were used required for the simultaneous detection of each of the four base termination ladders generated using the Sanger dideoxy method (Sanger, F., Nicklen, S., and Coulson, A. R., (1977) *Proc. Natl. Acad. Sci.* U.S.A. 74, 5463–5467) (Smith, L. M., Sanders, J. Z., Kaiser, R. J., Hughes, P., Dodd, C., Connell, C. R., Heiner, C., Kent, S. B. and Hood, L. E., (1986) *Nature* 321, 674–679) (Prober, J. M., Trainor, G. L., Dam, R. J., Hobbs, F. W., Robertson, C. W., Zagursky, R. J., Cocuzza, A. J., Jensen, M. A. and Baumeister, K., (1987) *Science* 238, 336–341). In these studies, unique fluorescent labels were linked to the four different sequencing fragment ladders by either labeling the primer or the terminator used in the extension reaction with unique labels. Furthermore, U.S. Pat. No. 5,436,130 describes a DNA sequencing method which uses single slab gel lane or electrophoresis capillary. Sequencing fragments are separated in said lane and detected using a laserexcited, confocal fluorescence scanner. In this case, each set of DNA sequencing fragments is separated in the same lane and then distinguished using a binary coding scheme employing only two different fluorescent labels to uniquely label the four sets of sequencing fragments. Also described is a method of using radio-isotope labels to similarly code or label the fragments. For DNA sequencing applications, it would clearly be valuable to develop methods for multiplex electrochemical labeling, separation and detection. It would also be valuable to develop analogous methods for the multiple labeling of DNA fragments to be used in DNA diagnostics employing RFLP, STR or SNP assays and the like. The simultaneous detection of multiple labels in a CE-EC run requires the development of strategies which are capable of detecting the multiple electrochemical signals generated by such a system. Differences in redox potentials between different compounds can be exploited for selective measurements using EC detection. Traditional voltammetric methods have been widely used in the literature to exploit these differences (Kristensen, E. W., Kuhr, W. G., and Wightman, R. M., (1987) *Anal. Chem.* 59, p. 1752). But, these methods involve rapid scanning of the electrode potential, which leads to large background charging currents. Poor sensitivity is obtained due to high background noise caused by these large charging currents.

OBJECTS AND SUMMARY OF THE INVENTION

It is a general object of the present invention to provide a method and apparatus for simultaneous detection of multiple electrochemical signals using multiple electrodes.

It is another object of the present invention to provide a microfabricated CE chip having multiple electrodes with each electrode optimized for the detection of a specific label or analyte.

It is a further object of the present invention to provide a method and apparatus for multiplex labeling and electrochemical detection of multiple analytes.

It is a still further object of the present invention to provide a method for attaching redox labels to analytes, electrophoretically separating the analytes and electrochemically detecting the individual separated analytes.

Another object is achieved by developing methods to label multiple analytes with different EC-labels that can be distinctly detected.

The foregoing and other objects of the invention are achieved by a microfabricated electrophoresis chip which includes a separation channel which widens into a detection reservoir with a plurality of thin film detecting or working electrodes extending into said detection reservoir closely adjacent the end of the separation channel. Another object of the invention is achieved by a method of simultaneously detecting electrochemical signals generated at said detection electrodes by different redox labels attached to analytes in a mixture of analytes after the analytes have been separated in the electrophoresis chip.

Another object is the method of multiplex electrochemical labeling and coding of various analytes to simultaneously distinguish multiple analytes simultaneously.

An additional object is to develop separation, detection and labeling methods for performing genotyping and sequencing with electrochemical detection.

BRIEF DESCRIPTION OF THE DRAWINGS

The foregoing and other objects of the invention will be more clearly understood from the following description when read in conjunction with the accompanying drawings in which:

FIG. 2 shows the redox potentials for some hydroquinone/quinone derivatives used as labels for electrochemical detection. (*CRC Handbook Series in Organic Electrochemistry*, Vol. 1–5, Eds. Mertes, Zuman, Scott, Campbell, Kardos, Fenner, Rupp, CRC Press, Inc.)

FIG. 3 shows the coding format for selective electrochemical detection of multiple labels employing two oxidative and two reductive labels. Here $|V_2|>|V_1|$ and $|V_4|>|V_3|$.

FIG. shows the synthesis scheme for labeling DNA with a redox-active label to make the conjugate electroactive.

Figure 8:
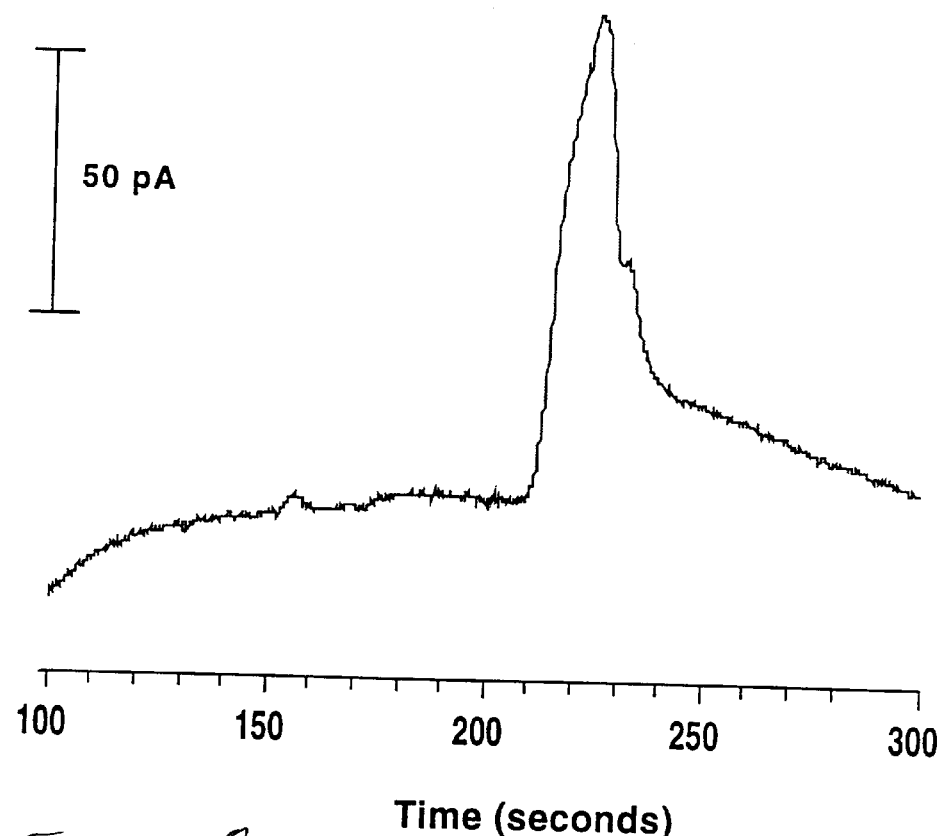

FIG. 8 shows capillary electrophoresis electrochemical detection of an M-13 DNA-primer tagged with 1,4-dihydroxy-2-naphthoic acid using an electrochemical chip.

Figure 9:
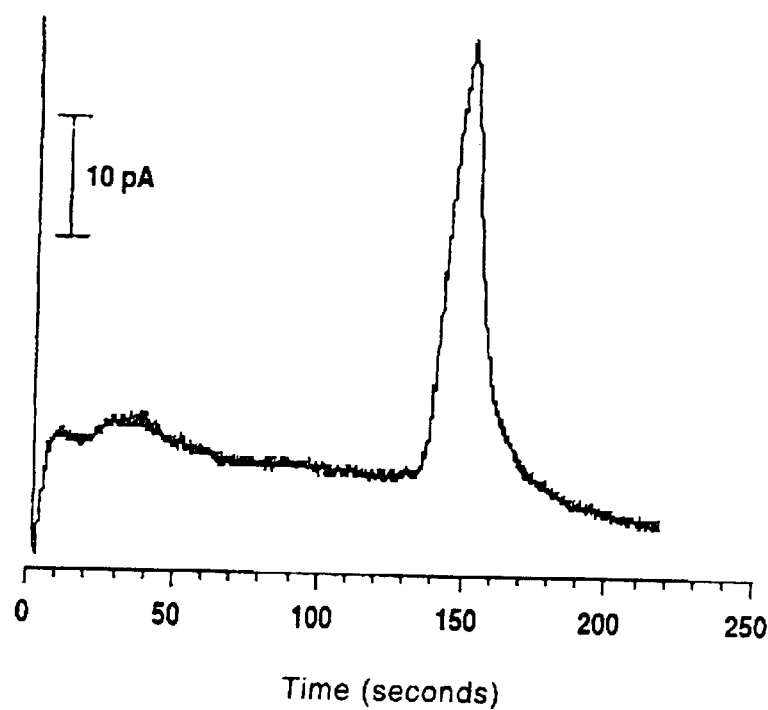

FIG. 9 shows the capillary gel electrophoretic separation and EC-detection of a PCR product obtained after amplification by using an EC-labeled M-13 primer. The product was separated in an EC-CE chip using 0.75% HEC as the separation matrix.

Figure 10A:
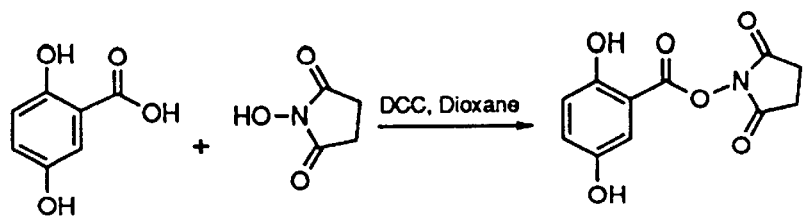
Figure 10A:
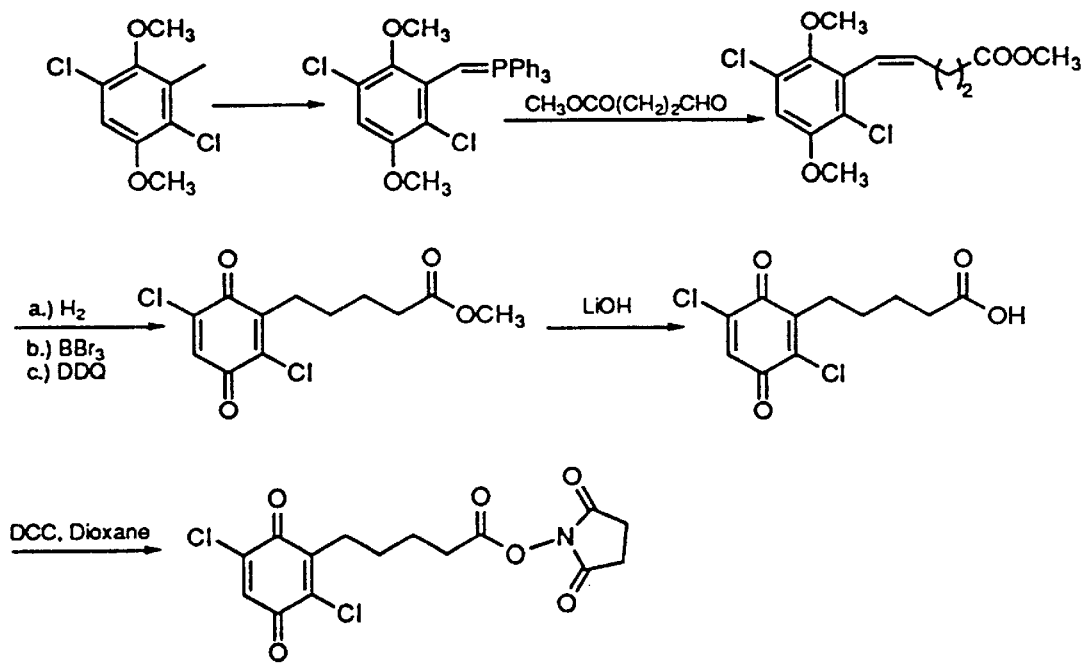
Figure 10A:
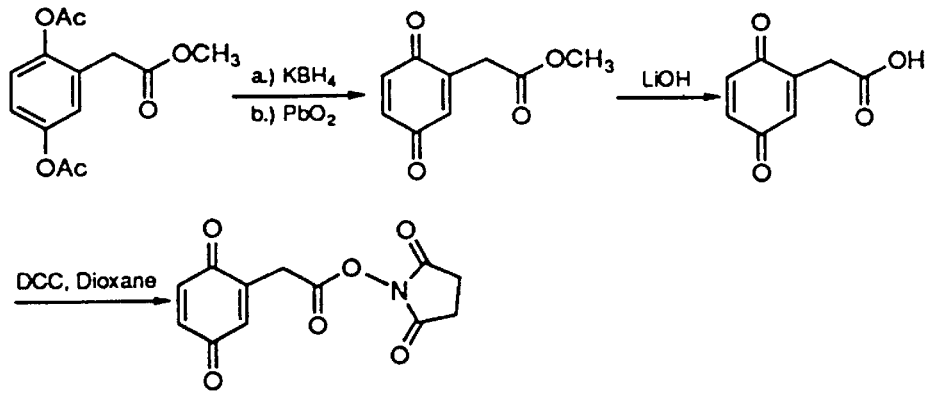
Figure 10:
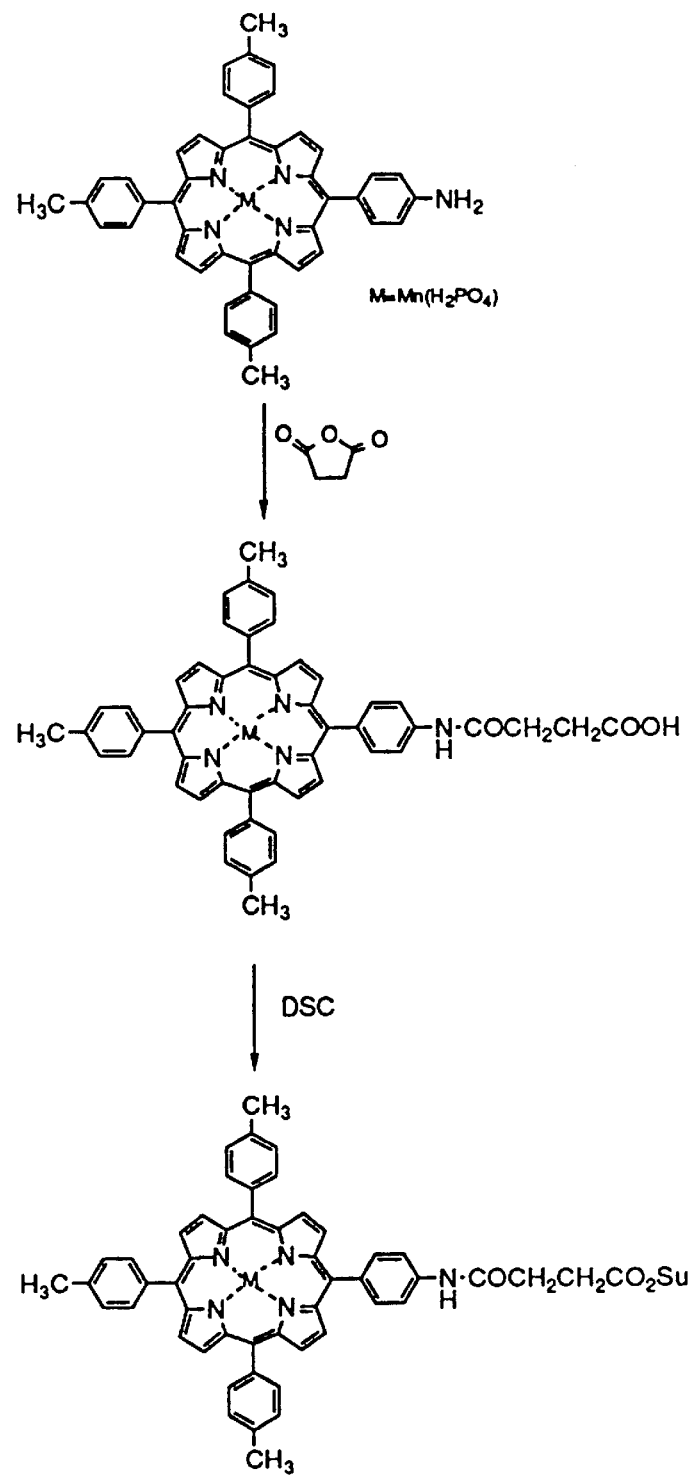

FIG. 10A shows proposed synthetic routes to the active esters of redox-active labels of quinone or hydroquinone derivatives for electrochemical detection.

FIG. 10B shows proposed synthetic routes to the active esters of redox-active labels of metalloporphyrins for multiplex electrochemical detection.

Figure 1:
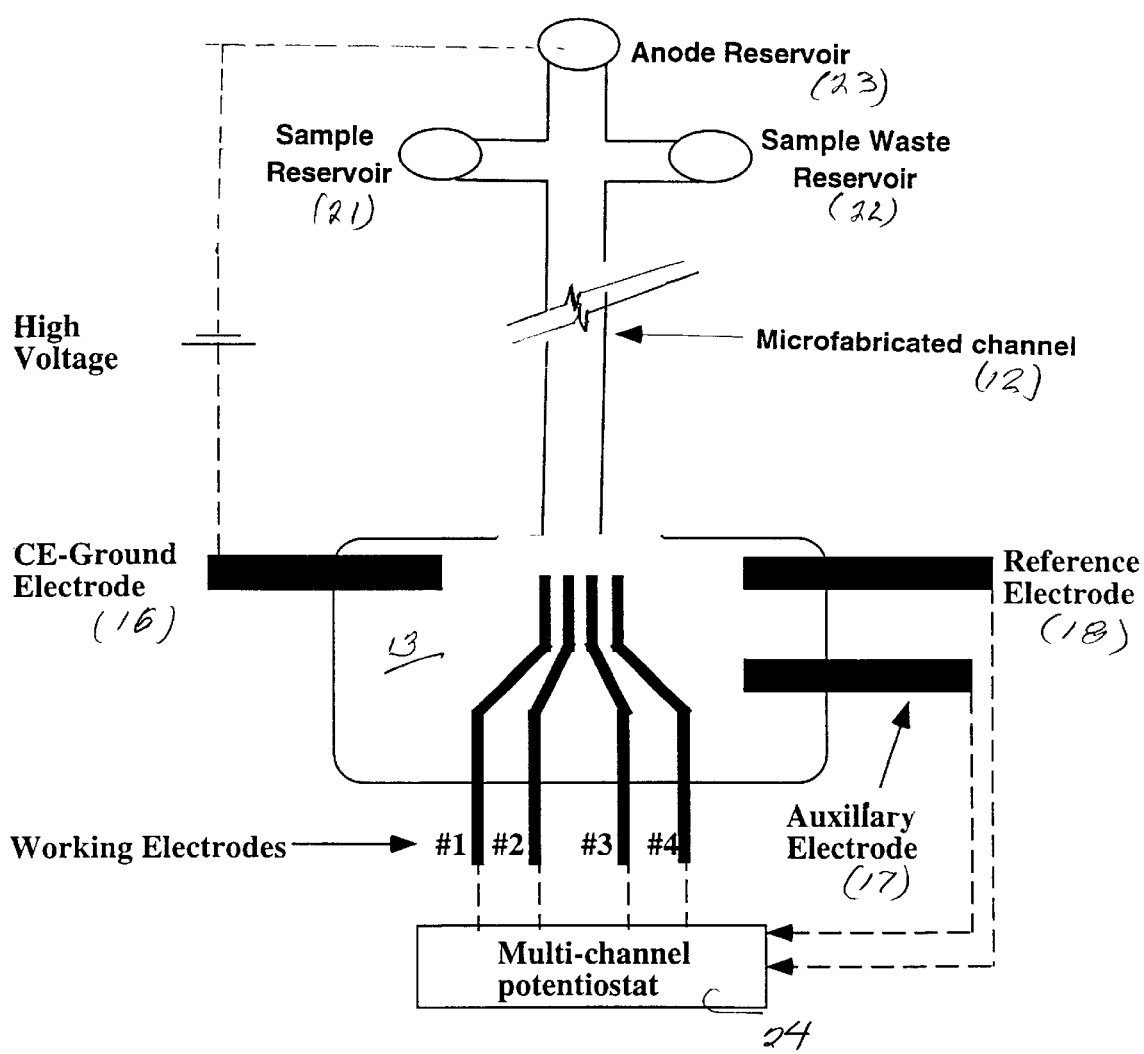
FIG. 1 shows a microfabricated capillary electrophoresis chip in accordance with one embodiment of the present invention.
Figure 11:
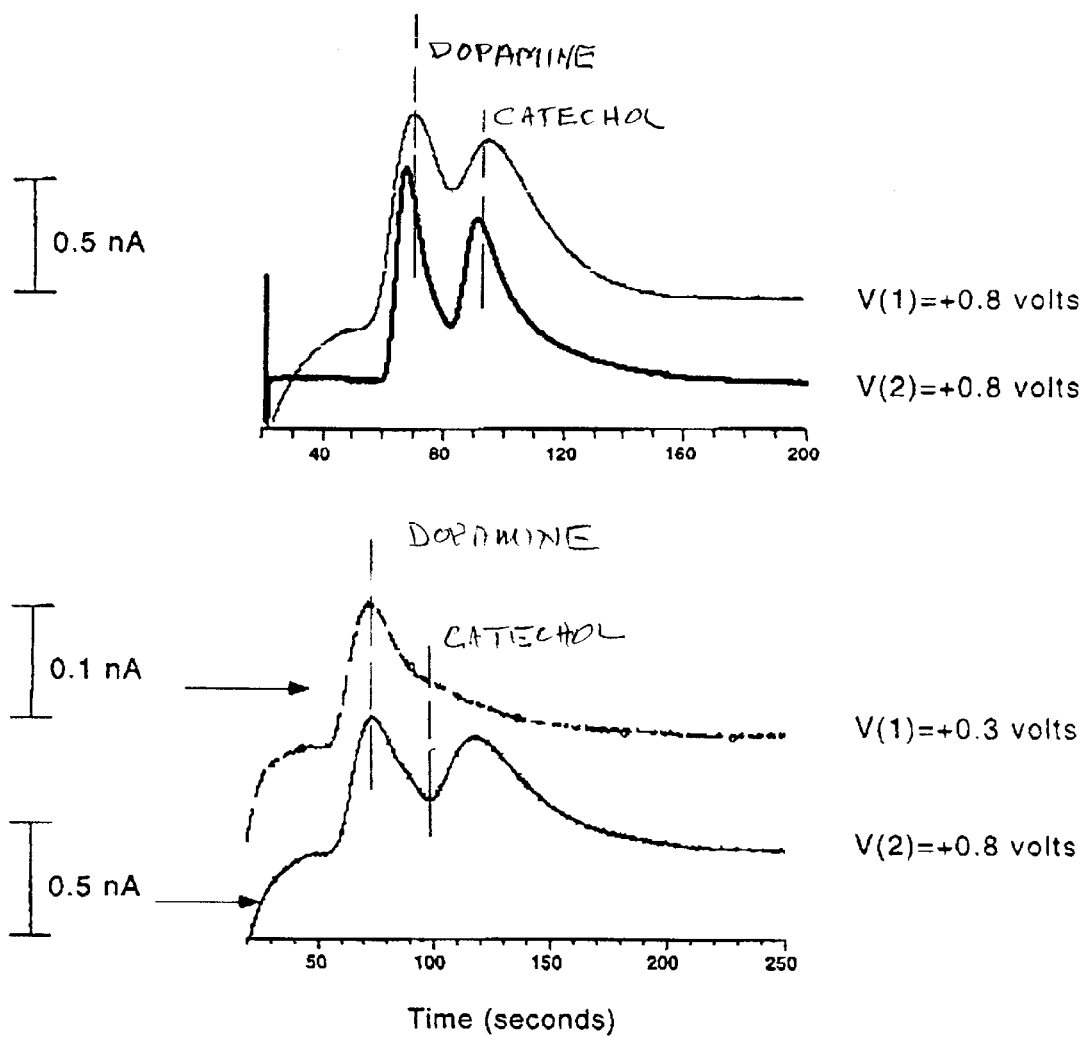

FIG. 11 shows multiplex detection of two analytes simultaneously using an electrochemical chip of the design shown in FIG. 1.

Figure 12:
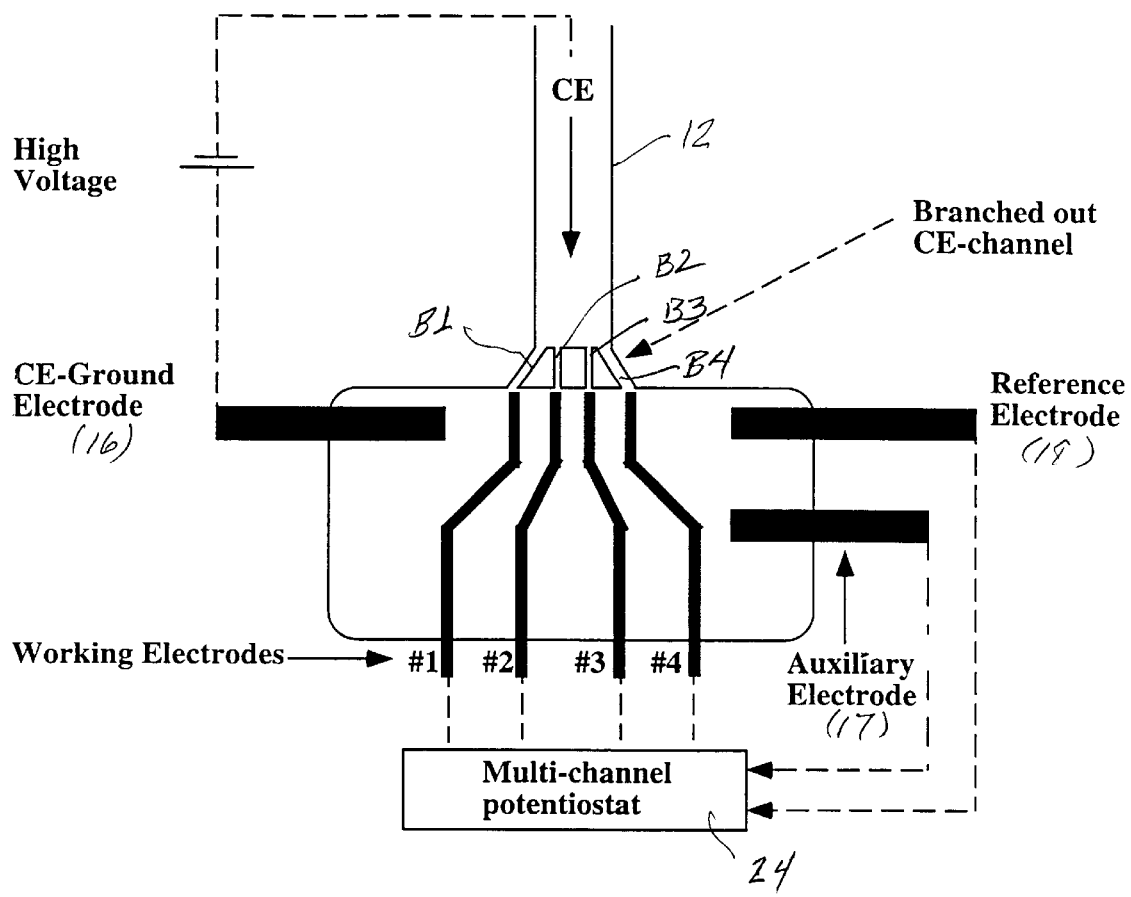

FIG. 12 shows a microfabricated capillary electrophoresis chip in accordance with another embodiment of the present invention.

DESCRIPTION OF THE PREFERRED EMBODIMENTS

There is described a novel approach for highly selective multiplex labeling and electrochemical detection of multiple analytes. Redox labels can be attached to all possible analytes such as DNA, RNA, nucleotides, peptides and proteins, carbohydrates and amino acids, etc. The labeled analytes are detected in conjunction with a separation method. The separation method can be CE, capillary zone electrophoresis (CZE), micellar electrokinetic chromatography (MEKC), isoelectric focusing (WEF), isotachophoresis (ITP), liquid chromatography (LC), high performance liquid chromatography (HPLC), capillary electrochromatography (CEC), capillary gel electrophoresis (CGE), and any other form of electrophoretic or chromatographic separation. We also illustrate an approach to attach redox-active labels to oligonucleotides, but other synthetic routes can be used which have been described in the literature for the attachment of redox-active or other labels to other molecules. Specifically, three or four different electrochemical labels are used to demonstrate the concept of selective electrochemical detection of label:target conjugate such as those needed for the detection and identification of the four sets of base ladders in a DNA-sequencing run. A matrix based coding scheme is described which is capable of detecting the multiple signals simultaneously and uniquely identifying the labels based on their matrix value. This coding scheme can be used with a variety of redox-active labels which differ from each other in terms of their redox-active potentials and/or reaction kinetics at an electrode surface. The method is illustrated by detecting redox labels under electrophoretic conditions using a CE-channel with integrated electrochemical detection. The coding method can be used in a similar manner for the detection and identification of other redox labels, or for the detection of unlabeled analytes if they have distinctive redox properties. Novel CE-EC chip designs are described which can be microfabricated so as to exploit these differences between redox-active labels for the simultaneous detection of multiple analytes during a separation.

One area of genetic analysis where such multiplex DNA sequences containing di-, tri-, tetra-, and pentanucleotide repeats are often genetically polymorphic. EC labeling and analysis would be useful in the analysis of short tandem repeats or STRs. Over 2000 of these short tandem repeat (STR) polymorphisms have been mapped on the human genome, and it is estimated that thousands more remain to be discovered. Because of the abundance of this type of polymorphism and the relative ease of STR detection following amplification by the polymerase chain reaction (PCR). STRs have found widespread use as markers in gene mapping studies and are emerging as potential markers for use in testing for paternity and personal identity. The analysis of multiple STR markers against a size standard in gene mapping and in the development of population polymorphism data banks can be performed by multiplex redox labeling of the primer(s) used in the PCR step and electrochemical detection to be described. Similar primer labeling techniques could also be used in restriction fragment length polymorphism (RFLP) genotyping or in various types of labeled polynucleotide ligation assays. It is also possible to use uniquely electrochemically labeled fragment ladders as size standards to type unknown nucleic acid fragments where the size standards are generated with PCR using EC-labeled primers or nucleotides.

The Sanger dideoxy chain termination method (Sanger et al., *Proc. Natl. Acad. Sci.* 74, 5463–5467 (1972)) is an accepted technique for large-scale sequencing projects. The primers or terminators can be labeled with redox labels, and used to generate all possible fragments of the DNA template to be analyzed, where the fragments terminating with four different bases (A, C, G, T) are separated and simultaneously electrochemically identified by their different redox potential. Multiplex redox labeling and electrochemical detection can be used in conjunction with other methods of genotyping such as RFLP analysis, microsatellite analysis, and single nucleotide polymorphism (SNP) analysis all of which use primers or terminators for labeling and determining genetic variation. Since the methods used for the performance of RFLP, STR, oligonucleotide ligation assay, and single nucleotide polymorphism typing (which is essentially sequencing) allow, the incorporation of either labeled primers, labeled bases or labeled terminators, one can immediately see how to utilize electrochemically active labels to perform all of these classes of assays.

In accordance with one aspect of the invention, a 4"-glass wafer 11 was etched to form a CE separation channel 12 and detection reservoir 13. In one example, the channel was 33 $\mu$m wide and 14 $\mu$m deep. A platinum (Pt) layer of ~1000 Angstrom thickness was sputtered on the whole wafer by RF sputtering, and then patterned using standard photolithography. The exposed Pt-layer was then etched using hot aqua-regia (3:1, HCl:HNO$_3$), leaving behind the Pt pattern which was protected by hard-baked photoresist. The photoresist was subsequently removed to expose the desired electrode pattern as shown in FIG. 1. The pattern included a Pt CE-ground electrode 16, working electrodes 1–4, auxiliary electrode 17, and reference electrode 18. The working electrodes were 10 $\mu$m wide, spaced 5 $\mu$m apart, and preferably placed 20 $\mu$m away from the outlet of the CE-channel. The working electrodes may be as much as 500 $\mu$m from the end of the channel although preferably they are less than 100 $\mu$m from the end of the channel. The principle behind the isolation of the working electrodes from the CE-current without any significant loss of ability to detect the analytes eluting from the separation column has been described previously (Woolley, A. T., Lao, K., Glazer, A. N. and Mathies, R. A., (1998) *Anal. Chem.* 70, 684–688) (Mathies, R. A., Glazer, A. N., Woolley, A. T., and Lao, K., (1996) U.S. patent application Ser. No. 703,394; filed Aug. 26, 1996, Electrochemical Detector Integrated on Microfabricated Capillary Electrophoresis Chips and continuation-in-part Ser. No. 08/916,557 filed Aug. 22, 1997). Briefly, the separation channel widens into a detection reservoir which is 10–100 times wider than the channel. The electrophoresis current is grounded instantaneously as it enters this reservoir due to the large increase in area and reduced solution resistance. Interference from the electrophoresis current is minimized by placing the working electrodes 20 μm from the point of widening. Diffusional loss of analytes is minimal due to the close placement of the working electrodes to the outlet end of the channel. Consequently, the analyte concentration detected at the working electrodes is still high, whereas the pickup from the electrophoresis current is minimized.

In the experiments to be described, all separations were performed under identical conditions of capillary zone electrophoresis with a microfabricated electrophoresis chip having a single working electrode unless specified otherwise. Injection was performed by applying +400 volts for 40 seconds at the sample reservoir 21, and grounding the sample waste reservoir 22, while floating the anode 23 and detection reservoirs. The voltages were then switched for the separation by applying a high positive voltage of +400 volts at the anode reservoir, and keeping the reservoir at the detection end (cathode) grounded. The sample and sample waste reservoirs were back-biased by applying +300 volts to each during the run. All separations were performed using 25 mM morpholino-ethane-sulfonic acid (MES, with 1 mM $Cl^-$, pH=5.65) as the separation buffer.

All potentials were relative to the reference electrode 18, and were applied by using a low-noise potentiostat 24 (Low-current module, BioAnalytical Systems, Ind.). The signals were collected by the same potentiostat, and digitized at a sampling rate of 5 Hz using LabView software and a DAQ-1200 card (National Instruments, Tex.) on an Apple Macintosh PowerBook 1400c.

Quinones and hydroquinones were chosen as examples of labels for initial separations as they have been widely used as model compounds in electrochemical studies of biological redox processes, so their electrochemical properties are well known. (*Enzyme and Metabolic Inhibitors*, J. L. Webb, Academic Press, N.Y., Vol. 3, pp. 421–594 (1966)) These compounds are advantageous because they are readily available, easily handled under ordinary experimental conditions, exhibit uncomplicated electrochemical reactivity, and represent a wide range of structures and chemical properties. The redox potentials of these compounds are dependent on various substituents, heterocyclic aromaticity, ring strain and the solvent. The ability to modulate the redox potential by altering the chemical structure provides a way of generating families of very closely related compounds with appropriately spaced redox potentials. FIG. 2 highlights a list of various quinoid redox labels with different redox potentials $E_p$ in organic solutions such as MECN or ETOH. Four labels, namely, 1,4-dihydroquinone (1), 1,4-dihydroxy-2-naphthoic acid (2), 1-methyl, 4-benzoquinone (3), and 2,5-dichloro-1,4-benzoquinone (4) were chosen as they are detected at significantly different potentials. 1 and 2 are detected at positive (or oxidative) potentials of +0.46 and +0.23 volts, and 3 and 4 are detected at negative (or reductive) potentials of –0.58 and –0.18 volts, respectively under the particular experimental and solvent conditions used to generate the tabulated values.

In order to minimize any possibility of cross-talk between different detection channels, the detection potentials of the labels are chosen such that they differ from each other by greater than 200 mV. Due to the use of two oxidative and two reductive labels, a matrix coding method is used to interpret these signals as illustrated in FIG. 3. The signals at an oxidative electrode for a particular label are categorized as "positive high (+1) or low (0)", depending on whether a significant signal is seen above the background at that potential. Reductive signals (which are of opposite polarity) are characterized as "negative high (or –1) and low (0)", again depending on whether significant signal is seen above the background at that potential. The label with the higher oxidation potential ($V_2$) is detected at only the most oxidative electrode, so it is given the matrix code of (0,1). This is illustrated by label 1 in FIG. 3 that, under the particular conditions of this experiment, is oxidized at potential $V_2$ but is not oxidized at the electrode poised at the lower potential $V_1$. The other oxidative label with a lower oxidation potential $V_1$ is detected at both oxidative electrodes, therefore it is given the code (1,1). Analogously, the two reductive signals would be coded (0,–1) and (1,–1). Consequently, each of the labels has a unique "signed binary code" or matrix value, and therefore can be unequivocally identified. This coding method provides a way to decompose the detection signals from each other, thereby ensuring unique measurement of the electrochemical signals from the various labeled analytes.

Figure 4A:
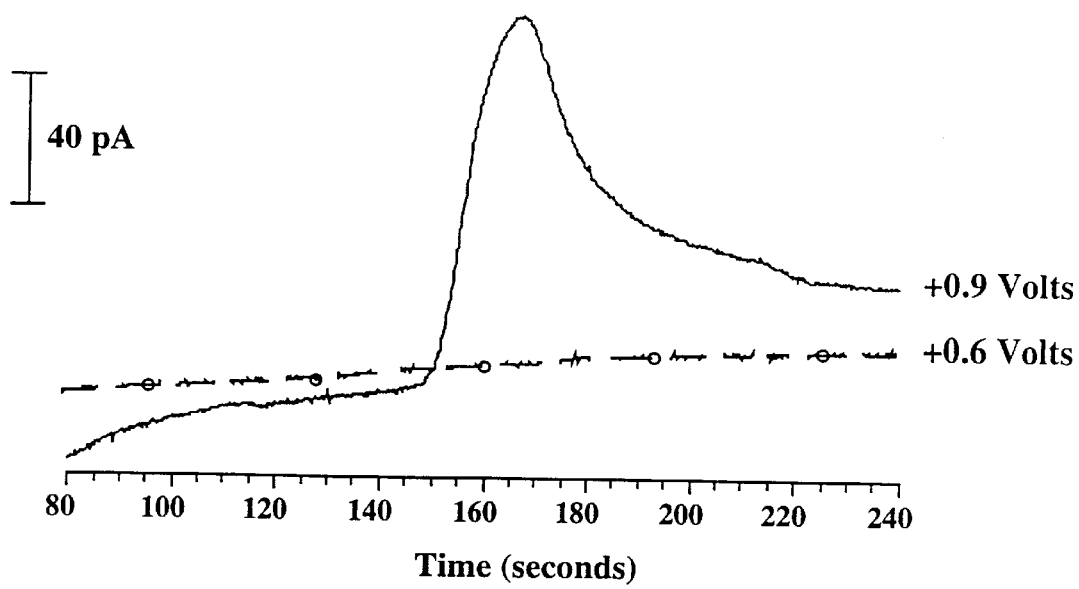
FIG. 4A shows selective electrochemical detection of 1 (1,4-dihydroquinone) at +0.9 volts vs. Ag/AgCl but not at 0.6 volts. The matrix value for 1 is (0,1).
Figure 4B:
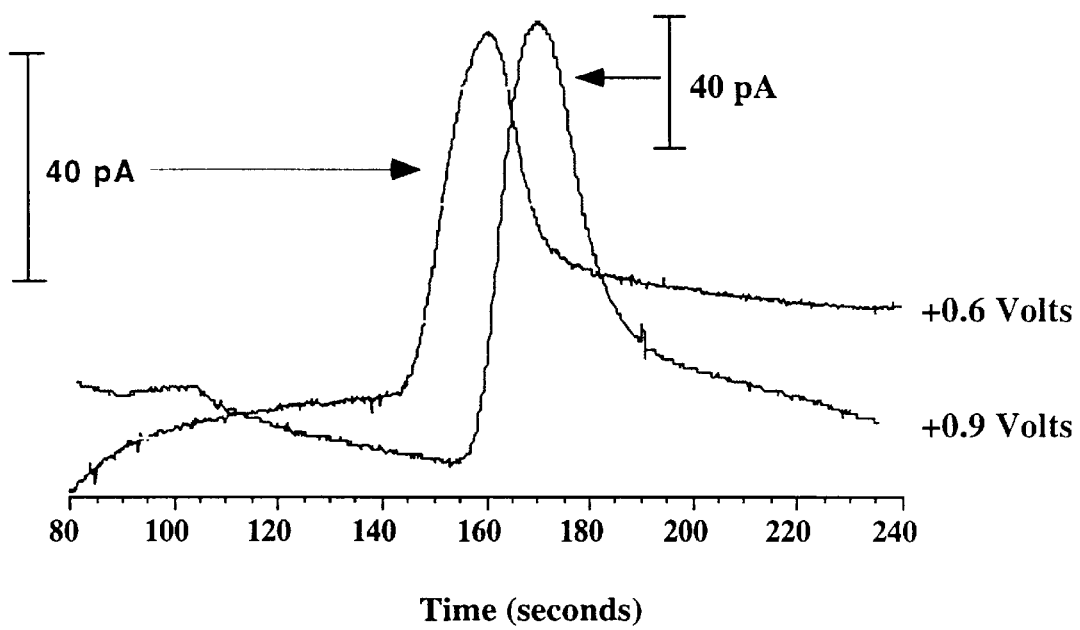
FIG. 4B shows electrochemical detection of 2 (1,4-dihydroxy-2-naphthoic acid) at both +0.6 and +0.9 volts. The matrix value for 2 is (+1,+1).

Selective electrochemical detection of two oxidative labels using this approach is shown in FIGS. 4A, 4B. 1 (1,4-dihydroquinone) and 2 (1,4-dihydroxy-2-naphthoic acid) are selectively detected using different electrode potentials. The analytes were injected into the CE channel and separated by capillary zone electrophoresis. For our experimental conditions, 1 is detected easily at a higher oxidative potential of +0.9 volts, but its signal is completely eliminated by lowering the electrode potential to below +0.6 volts, FIG. 4A. On the other hand, under the same conditions, 2 is very easily detectable at +0.9 volts, and also at +0.6 volts, FIG. 4B. Consequently, the two oxidative labels can be discriminated from each other by poising the electrode detecting 2 (only) at +0.6 volts ($V_1$), and the electrode detecting both 1 and 2 at +0.9 volts ($V_2$). These detection voltages are somewhat different from those predicted in FIG. 2 because of the different solvent and buffer experimental conditions. The matrix value for 1 is (0,1), as it is only detected at the high potential electrode, whereas the matrix value for 2 is (1,1) as it is detected at both electrodes.

Figure 5A:
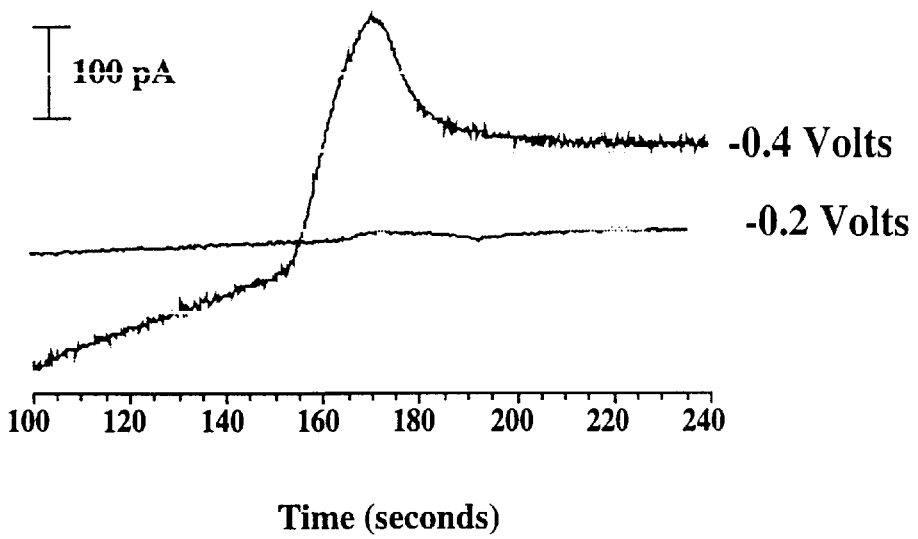
FIG. 5A shows selective electrochemical detection of 3 (methyl-1,4-benzoquinone) at −0.4 volts, but its signal is completely eliminated by lowering the potential below −0.2 volts. The matrix value for 3 is (0,−1).
Figure 5B:
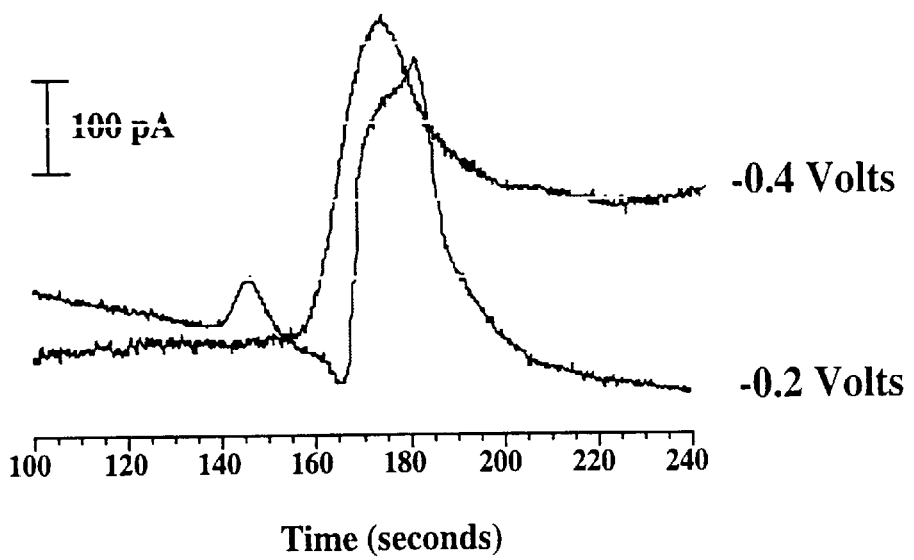
FIG. 5B shows selective electrochemical detection of 4 (2,5-dichloro-1, 4-benzoquinone) at both −0.2 and −0.4 volts. The matrix value for 4 is (−1,−1).

A similar approach is demonstrated for selective detection of reductive labels as shown in FIGS. 5A, 5B. Under our experimental conditions, 3 (1-methyl, 4-benzoquinone) is detected only at –0.4 volts or above, whereas, 4 (2, 5-dichloro-1,4-benzoquinone) is detected easily at –0.2 volts and –0.4 volts. The two labels are thereby discriminated by poising one electrode at –0.2 volts for the detection of 4 only and the other electrode at –0.4 volts for the detection of both 3 and 4. The matrix value for 3 is (0,–1) as it is only detected at the most negative electrode, but a value of (–1,–1) codes for 4 as it is detected at both reductive electrodes. As the four labels have unique matrix values, they are uniquely coded and consequently identified with certainty.

Figures 6, 7:
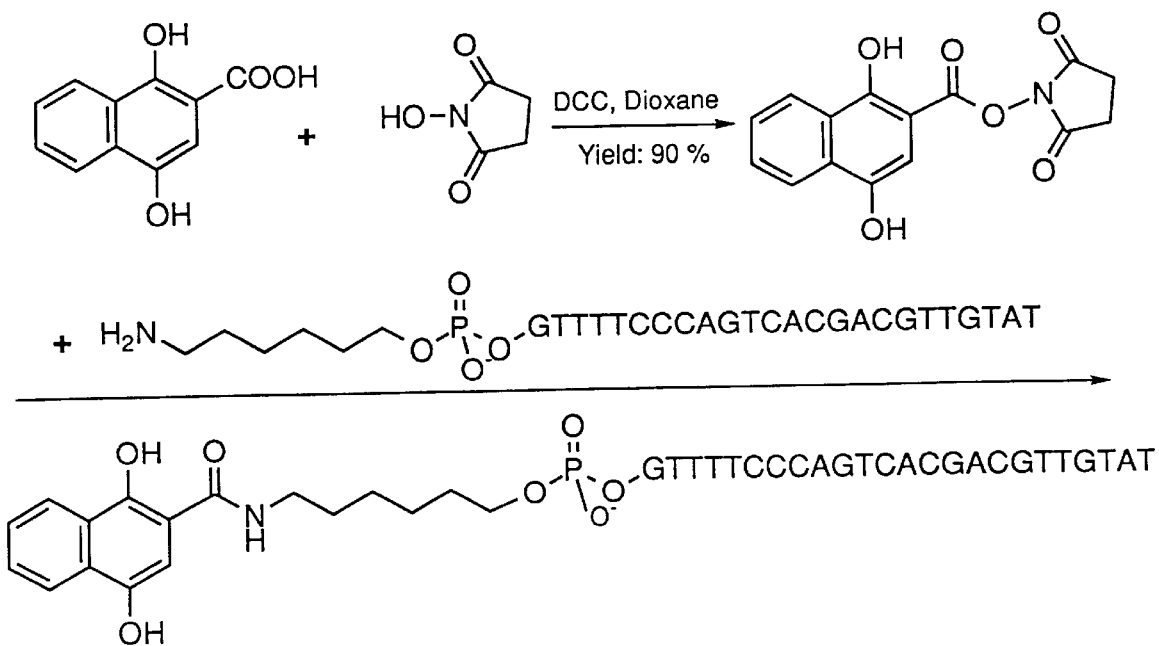
FIG. 6 shows the coding format for selective electrochemical detection of multiple labels employing four oxidative or four reductive labels. Here $|V_1|<|V_2|<|V_3|<|V_4|$.

Other combinations of labels can be used with this coding scheme. For example, four oxidative (or four reductive) labels can be used, where the labels each react at different redox potentials. FIG. 6 depicts the matrix values that apply for the oxidative case. The values are still unique to each label, thereby allowing complete identification of the multiple signals. This detection strategy is easily scaled for any number of electrochemical labels which need to be detected in a single separation. "N" analytes can be detected by attaching "N" different labels (both oxidative and reductive) to the analytes. Selectivity can generally be achieved between labels which are designed such that their redox potentials are approximately 60 mV or more apart (Bard, A.

J. and Faulkner, L. R., (1980) *Electrochemical Methods-:Fundamentals and Applications*, New York, John Wiley and Sons). Therefore, analyses of multiple samples in a mixture can be accomplished after synthesis of appropriate labels for each sample conjugating the label with the desired target, and detecting the coded label:target conjugates.

Another approach for selective electrochemical detection is to design redox labels with different heterogeneous electron transfer rate constants at an electrode surface ($k^o$). Most electrodes only offer a very limited potential window (generally between −1.0 to +1.0 Volts) for redox activity, thereby limiting the labels which can be used for selective detection via redox potential differences. But, the kinetics of the redox activity of molecules can easily vary from $10^{-6}$ to $10^{-9}$ cm$^2$/s at the various electrode surfaces. Thus, designing labels which have different $k^o$ values gives a much wider range of selectivity as compared to redox potential differences. This difference in $k^o$ can be easily exploited to selectively detect electroactive labels by using traditional voltammetric techniques. For example, four types of analytes can be detected by cycling four electrodes across the detection potential range at different scan rates. The different scan rates are chosen in increasing order such that one electrode matches the $k^o$ for the detection of one analyte each. The slowest reacting analyte (minimum $k^o$) is detected at only the slowest scanning electrode, and not at the other more rapidly scanning electrodes. The next slowest analyte is detected at the two slower scanning electrodes, and so on. Analogous coding schemes to those described in FIG. 6 for redox-potential based selectivity can be achieved in this case. But, as the sensitivity of these voltammetric techniques is at most in the micromolar concentration range, they may not be sensitive enough to detect low levels of analytes such as DNA sequencing products. In that case, sinusoidal voltammetric detection can be utilized, as it is capable of better selectivity and sensitivity in comparison to the traditional voltammetric detection (Singhal, P., Kawagoe, K. T., Christian, C. N., and Kuhr, W. G., (1997) *Anal. Chem.* 69, 1662–1668). This technique uses a large amplitude sinusoidal waveform to scan across a potential window on an electrode surface. Instead of the traditional approach of looking at the electrochemical signal versus time, this technique relies on the harmonic isolation and digital phase locking of electrochemical signals. It is at least two orders of magnitude more sensitive than constant potential detection, and up to four orders of magnitude more sensitive than cyclic voltammetric detection. Nanomolar levels of various carbohydrates (Singhal, P., Kawagoe, K. T., Christian, C. N. and Kuhr, W. G., (1997) *Anal. Chem.* 69, 1662–1668) and nucleotides (Singhal, P. and Kuhr, W. G., (1997) *Anal. Chem.* 69, 3552–3557), and picomolar levels of oligonucleotides and DNA (Singhal, P. and Kuhr, W. G., (1997) *Anal. Chem.* 69, 3552–3557) can be detected using this method. Another approach for enhancing the signal-to-noise in sequencing and genotyping applications that employ polymerase extension would be to use redox-labeled dNTPs in the extension or PCR reaction so that multiple labels are introduced into each fragment to be sized.

All the approaches described above require only one type of electrode material (platinum) to detect the redox-active labels. The use of other metals as electrodes can also be exploited to achieve selective detection. For example, copper electrodes have been shown to electrocatalytically oxidize both purine and pyrimidine base nucleotides (Singhal, P., and Kuhr, W. G., (1997) *Anal. Chem.* 69, 3552–3557). So, instead of using all four platinum electrodes in the case of DNA-sequencing, one electrode can be made out of copper. This electrode basically acts as a counter for the arrival of each DNA fragment at the detector end. Three other electrodes can then be used to detect three differently labeled bases. Such three-color combinatorial coding methods were recently described in detail by Kheterpal et al. (Kheterpal, I., Li, L., Speed, T. P. and Mathies, R. A., (1998) *Electrophoresis* 19, 1403–1414) and shown to be highly successful for fluorescence-based DNA sequencing. This approach therefore requires the synthesis of only three redox-active labels instead of the four labels required with the methods described earlier. This approach might produce a simpler labeling and detection method whose signals are more easily decomposed from one another.

Redox-active labels can be attached to various analytes of interest by a wide variety of synthetic approaches. Attachment of 2 (1, 4-dihydroxy-2-naphthoic acid) to a DNA-primer for an M-13 sample is highlighted as an example of the synthetic route used to tag redox-active labels to oligonucleotides in this work. The active N-hydroxysuccinimide ester of 2 was first synthesized by the scheme depicted in the top portion of FIG. 7. An electrochemically active DNA probe was then prepared by linking the active derivative with 5'-aminohexyl-terminated primer. The procedure involved the initial solid-phase preparation of the 5'-amino-functionalized primer oligonucleotide using traditional nucleoside phosphoramidite chemistry. This was followed by conjugation of the CPG solid-support oligonucleotide to the N-hydroxysuccinimide ester of 1,4-dihydroxy-2-naphthoic acid. Subsequent exposure of the support to aqueous ammonium hydroxide resulted in the release of the fully deprotected primer conjugate, which was purified by reverse-phase HPLC. FIG. 8 illustrates the sensitive detection of the M-13 primer after attachment of the hydroquinone label. The mass detection limit for this labeled analyte is in the zeptomole range, showing that the derivatization is not detrimental to the sensitive detection of the redox-active label. Also, as those labels are low-molecular weight compounds with no charge, their attachment does not cause any significant shift in the mobility of the analyte. This means that the existing separation conditions can be easily used for the labeled analyte without any degradation in the resolution and efficiency of the separation. Also, there is no need for difficult and imperfect software solutions for mobility shift correction when analyzing two different sets of DNA fragments that have been conjugated with different labels. Another advantage of these low molecular weight labels is that when conjugated to a primer they do not present any steric or other hindrances for the amplification of DNA fragments that the primer or oligonucleotide is hybridized to during the PCR or any other amplification, extension or ligation process. FIG. 9 shows the electrophoretic separation and detection of a 735 bp Anabena DNA fragment insert closed into a vector after PCR amplification with an M-13 forward primer labeled with redox label 1 and unlabeled M-13 reverse primer. Detection of this fragment illustrates that a redox labeled DNA primer can be used to amplify DNA using standard protocols currently used for the PCR, and analyzed using CE with EC detection. There is thus every reason to believe that redox-labeled primers, labeled-nucleotide triphosphates, labeled-dideoxy nucleotide triphosphates or labeled-oligonucleotides will be successful in performing DNA sequencing extension reactions with a wide variety of polymerases and/or in performing ligation followed by size analysis of the ligated fragments and/or in performing all types of PCR amplification or rolling circle amplification methods followed by size analysis of the amplified products.

In analogy with the above derivatization method, active N-hydroxysuccinimide esters of other redox-active labels can be synthesized and attached to 5'-aminohexyl-terminated DNA. FIG. 10(A) illustrates the synthetic routes for preparing active esters for labels 1, 3 and 4 used in this work. These redox active labels can also be attached to DNA chain terminators which provide many advantages. Thus only DNA sequencing fragments resulting from the redox-active terminators can be detected. Alkynylamino-nucleoside triphosphates have been reported as being useful as chain terminators in DNA sequencing (Habbs, F. and Cocuzza, A., 1987, U.S. Pat. No. 5,047,519). Redox-active alkynylamino-nucleoside triphosphates of A, G, C, T can be prepared via amide linkages by reacting the active N-hydroxylsuccinimide esters of redox-active labels with alkynylamine nucleoside triphosphates. Similar methods can be used to redox label dNTPs that have a 3'-OH group and can thus be used in extension reactions. Furthermore, labeling is not limited to quinone/hydroquinone compounds. Active esters of other redox-active labels such as metalloporphyrins can be prepared as highlighted in FIG. 10(B). Various other compounds like RNA, PNA, peptides, proteins, carbohydrates, amino acids and other molecules can also be labeled with electrochemical labels by using a wide variety of synthetic schemes for conjugation of labels described extensively in the literature. (*Bioconjugate Techniques*, G. 7. Hermanson, Academic Press, N.Y. (1996)). These compounds can subsequently be detected using the CE-EC chip based system and the coding scheme described above. FIG. 11 shows an example of the detection of two analytes simultaneously using this concept. A CE-EC chip similar to that described in FIG. 1 was used, but with only two working electrodes. At +0.8 volts both dopamine and catechol were then detected at both the working electrodes after a CZE separation. The two electrodes were poised at different potentials to selectively detect these two analytes simultaneously. In this case, only dopamine was detected at electrode #1 which was now poised at a lower potential of +0.3 volts. Both dopamine and catechol are still detected at electrode #2 which is poised at +0.8 volts. Thus, for catechol, the matrix value is (0,1), while for dopamine the matrix value is (1,1). This work directly demonstrates that multiplex detection can be achieved using CE-EC chips by microfabricating multiple working electrodes outside a CE-channel.

FIG. 12 shows a microfabricated chip as in FIG. 1, except that it employs branched separation channels. Like reference numerals have been applied to like parts. In this embodiment, the single CE-channel is branched just before the outlet end into a number of small branches B1, B2, B3, B4. The number of branches corresponds to the number of electrochemical labels being detected. A detection electrode 1, 2, 3 or 4 is microfabricated at the outlet of each branch, which serves as the detector for the eluent from that particular branch. In this manner, each electrode can be poised for the detection of only one analyte from the eluent buffer stream in each channel branch. This minimizes diffusional and electrical cross-talk between the various electrodes as they can be placed far apart (>10–50 $\mu$m) from each other without any loss of analyte sensitivity.

Interference from high electrophoresis currents can lead to a variable drop in the voltage applied to the working electrode, known as IR drop (where I is the electrophoresis current, and R is the solution resistance between the working and the reference electrode). IR drop causes unpredictable shifts in the electrode potential and 5 consequently leads to higher background noise in the electrochemical signal. A reference electrode can be precisely and permanently positioned very close to the working electrode (~100–200 $\mu$m) by microfabrication. This minimizes any IR drop by decreasing the solution resistance significantly (as R is proportional to the distance between the working and the reference electrode). Integration of reference electrodes 10 also leads to a more robust CE-EC chip with more stable background signals.

Ag/AgCl reference electrodes can be integrated on CE-EC chips. Silver (Ag) can either be deposited directly or electroplated on to another metal which is deposited on the CE-EC chip. Direct deposition can be done by sputtering or other commonly used metal deposition techniques described in the literature. In the second approach, Ag can be electroplated on the Pt electrodes which are microfabricated as described above. A Pt electrode (besides the working, auxiliary and ground electrodes, etc.) can be microfabricated and converted to an Ag/AgCl electrode by electroplating. Pt is electroplated with Ag, which is subsequently oxidized in a chloride solution to yield a precipitate of AgCl over the plated Ag, thereby giving an Ag/AgCl electrode.

There is described a method for selectively labeling and detecting redox-active labels by using a "signed binary coding" scheme. The method allows selective detection of multiple labels simultaneously after an electrophoretic or chromatographic separation. A specific application with four different electroactive labels is detailed, which can be used to identify four different bases in DNA-sequencing by CE-EC. It is apparent that the method and the microchip can be adapted to any number of different electroactive labels by increasing the number of working electrodes. Additionally, the method is easily extended to RNA, PNA, peptides, proteins, amino acids, carbohydrates and other compounds as they can also be labeled with redox-active labels or, in select cases, where the analytes themselves have unique redox properties. Labeling with redox-active labels makes inherently non-electroactive compounds amenable to EC detection. Selectivity between various labeled analytes is achieved by discrimination between their redox-potentials and/or kinetics with which they react at an electrode surface. Signals are effectively distinguished from each other by using a coding matrix, with each label having a unique matrix value. This method insures a very accurate approach for the simultaneous detection and identification of multiple electrochemical labels. Thus, detection of multiple analytes in a single separation can be done with very high selectivity and confidence and without the drawbacks of optical detection. Also described is a microfabricated capillary electrophoresis chip for carrying out the present invention. However, it should be apparent that the selective labeling and detecting method can be applied to other separation apparatus.

The foregoing description, for purposes of explanation, used scientific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A microfabricated capillary electrophoresis chip including a substrate with an elongated, narrow separation channel which widens into a detection reservoir and means for applying a separation voltage along the channel, two or more thin film working electrodes each adapted to receive a different working voltage extending into said detection reservoir opposite and near the end of said narrow separation channel where the working electrodes have minimal influence from the high electrophoresis potentials, said working electrodes simultaneously detecting current generated by molecules undergoing redox reaction as they migrate past the thin film electrodes after they have migrated down the channel and a ground electrode adapted to be connected to said means for applying a separation voltage along the channel and a reference electrode adapted to be connected to a reference voltage, both in said detection reservoir spaced from said working electrodes.

2. A microfabricated capillary electrophoresis chip as in claim 1 in which the elongated, narrow separation channel branches out to form multiple outlet channels each channel being opposite the end of a corresponding working electrode.

3. A microfabricated capillary electrophoresis chip as in claims 1 or 2 wherein the ends of the working electrodes are less than 100 $\mu$m from the end of the elongated separation channel.

4. A microfabricated capillary electrophoresis chip as in claims 1 or 2 wherein the ends of the working electrode are less than 1,000 $\mu$m from the end of the channel.

5. A microfabricated capillary electrophoresis chip as in claims 1 or 2 in which the separation channel is filled with a gel.

6. A microfabricated capillary electrophoresis chip as in claims 1 or 2 in which the channel is filled with a chromatographic separation medium.

7. A microfabricated capillary electrophoresis chip as in claims 1 or 2 in which the ground electrode and reference electrode are thin film electrodes.

8. A method of selective electrochemical detection of analytes in a complex mixture of analytes which comprises the steps of:
   labeling each analyte in the mixture with a redox label which generates an electrochemical signal which is different from the label attached to other analytes,
   separating the mixture to provide individual labeled analytes, and
   simultaneously detecting with two or more working electrodes the different electrochemical signals generated by the redox labels on the separated analytes to identify the individual analytes.

9. The method as in claim 8 in which the different electrochemical signals are detected by simultaneously applying different voltages to individual working electrodes and detecting oxidation and/or reduction of the redox labels.

10. The method as in claim 8 in which the different electrochemical signals are detected on the basis of different heterogeneous electron transfer rate constants of different analytes at a plurality of electrodes.

11. The method as in claim 8 in which the different electrochemical signals are detected by simultaneous voltammetric detection of the electrochemical signals at a plurality of electrodes.

12. The method as in claim 8 in which the different electrochemical signals are simultaneously detected by sinusoidal voltammetric detection of electrochemical signals at a plurality of electrodes.

13. The method as in claim 8, 9, 10, 11 or 12 in which the analytes are electrophoretically separated.

14. The method as in claim 8, 9, 10, 11 or 12 in which the analytes are chromatographically separated.

15. The method of selective electrochemical detection of analytes in a complex mixture of analytes which comprises the steps of:
   labeling each analyte in the mixture with a redox label which generates an electrochemical signal which is different from the label attached to other analytes,
   separating the mixture to provide individual labeled analytes, and
   simultaneously detecting the different electrochemical signals generated by the redox labels on the separated analytes to identify the individual analytes.

16. The method as in claim 15 in which the different electrochemical signals are detected by applying different voltages to at least one working electrode in the mixture and detecting oxidation and/or reduction of the redox labels.

17. The method as in claim 15 in which the different electrochemical signals are detected on the basis of different heterogeneous electron transfer rate constants of different analytes at said at least one electrode.

18. The method as in claim 15 in which the different electrochemical signals are detected by simultaneous voltammetric detection of the electrochemical signals at said at least one electrode.

19. The method as in claim 15 in which the different electrochemical signals are simultaneously detected by sinusoidal voltammetric detection of electrochemical signals at said at least one electrode.

20. The method as in claim 15, 16, 17, 18 or 19 in which the analytes are electrophoretically separated.

21. The method as in claim 15, 16, 17, 18 or 19 in which the analytes are chromatographically separated.

22. A method of electrochemically detecting individual analytes in a mixture of analytes comprising the steps of:
   labeling each analyte in the mixture with a redox label which generates an electrochemical signal which is different from the label attached to other analytes,
   separating the mixture in an electrophoretic separation channel,
   placing two or more electrochemical detection electrodes at or near the end of said separation channel, and
   simultaneously detecting the different electrochemical signals generated by the redox labels at each of said one or more detection electrodes to uniquely identify the individual labeled analytes.

23. The method of electrochemically detecting individual analytes in a mixture of analytes as in claim 22 in which the mixture of analytes comprises four analytes and in which two of the analytes are labeled with oxidative labels and two with reductive labels.

24. The method of electrochemically detecting individual analytes in a mixture of analytes as in claim 22 in which the mixture comprises four analytes and in which the four analytes are labeled with four different oxidative or reductive labels.

25. The method of detecting individual analytes in a mixture of analytes as in claim 22 in which there is one electrochemical detection electrode for each analyte in the mixture.

26. A method of determining the sequence of a DNA template which comprises the steps of:

generating and redox labeling all possible complementary sequencing fragments of the DNA template to be sequenced where the sets of fragments terminating with the four different bases (A, C, G, T) are identified by distinct electrochemical signals generated by the redox label associated with each of the distinct sets or fragments, electrophoretically separating said sets of labeled fragments in a single channel or lane, and simultaneously detecting the distinct electrochemical signals generated by the redox labels to identify the individual fragments.

27. The method as in claim 26 in which the fragments are generated with the dideoxy termination method employing primers or terminators, and the primers or terminators are labeled with the redox labels.

28. The method as in claim 26 in which the different electrochemical signals are detected by detecting analytes based on different heterogeneous electron transfer rate constants at a plurality of electrodes, one electrode for each fragment in the mixture.

29. The method as in claim 26 in which the different electrochemical signals are detected by simultaneous voltammetric detection of the electrochemical signals at a plurality of electrodes.

30. The method as in claim 26 in which the different electrochemical signals are simultaneously detected by sinusoidal voltammetric detection of electrochemical signals at a plurality of electrodes.

31. The method as in claim 26 in which two of the primers or terminators are labeled with oxidative redox labels and two are labeled with reductive redox labels.

32. The method as in claim 26 in which each of the four primers or terminators are labeled with different oxidative or reductive redox labels.

33. The method as in claim 26 in which different hydroquinone derivatives are attached to a DNA-primer, terminator or nucleotide triphosphates to make the sets of sequence fragments electroactive.

34. The method as in claim 26 in which sequence fragments are generated with the dideoxy chain termination method and the 3'-OH nucleotide triphosphates used for the chain extension are labeled with electrochemical labels.

35. A method of performing nucleic acid genotyping using electrochemical detection comprising the steps of:

labeling each nucleic acid analyte in a mixture with a unique redox active label which generates an electrochemical signal which is different from the labels attached to the other analytes, electrophoretically separating the mixture in a gel-filled capillary or channel, placing two or more electrochemical detection electrodes at or near the end of said separation capillary or channel, and simultaneously detecting the different electrochemical signals generated by the redox labels at each of said detection electrodes to uniquely identify the individual labeled analytes.

36. The method of claim 35 where the nucleic acid analytes to be genotyped are generated through the polymerase chain reaction using a forward and a reverse primer at least one of which is labeled with a unique electrochemical label.

37. The method of claim 36 where the amplified and labeled nucleic acid analyte is digested with a restriction enzyme to make labeled and restricted fragments for genotyping.

38. The method of claim 36 where the nucleic acid analytes to be genotyped are short tandem repeat fragments.

39. The method of claim 36 where the redox labels are different hydroquinone derivatives.

40. The method of claim 36 where the different electrochemical signals are detected based on different heterogenous electron transfer rate constants.

41. The method of claim 35 where the labeled nucleic acid analytes are generated by ligating two oligonucleotides in a complementary-template mediated reaction where at least one of the oligonucleotides to be ligated is labeled with a unique redox active label and the presence of the ligated and labeled nucleic acid analyte is diagnostic of the presence of the complementary template sequence.

42. The method of claim 35 where the labeled nucleic acid analyte is generated by performing a primer and template mediated extension reaction with a polymerase using either a redox labeled primer or a redox labeled terminator or a redox labeled nucleotide triphosphate and the determination of a the identity of a particular base in the template sequence defines a single nucleotide polymorphism.

43. A method of selective electrochemical detection of analytes in a complex mixture of intrinsically redox active analytes which comprises the steps of:

electrophoretically separating the mixture in a capillary or channel, placing two or more electrochemical detection electrodes at or near the end of said separation capillary or channel, and simultaneously detecting the different electrochemical signals generated by the redox active analytes at each of said detection electrodes to uniquely identify the individual analytes.

44. The method as in claim 43 in which the different electrochemical signals are detected by detecting analytes based on different heterogeneous electron transfer rate constants at a plurality of electrodes, one electrode for each fragment in the mixture.

45. The method as in claim 43 in which the different electrochemical signals are detected by simultaneous voltammetric detection of the electrochemical signals at a plurality of electrodes.

46. The method as in claim 43 in which the different electrochemical signals are simultaneously detected by sinusoidal voltammetric detection of electrochemical signals at a plurality of electrodes.

* * * * *